United States Patent [19]

Krieg et al.

[11] Patent Number: 5,305,887
[45] Date of Patent: Apr. 26, 1994

[54] METHOD AND APPARATUS FOR EXAMINING THE GASEOUS CONTENT OF RETURNED DRINK BOTTLES

[75] Inventors: Gunther Krieg, Im Rennich 12, 7500 Karlsruhe 41; Karl Koukolitschek, Karlsruhe; Wilfried Maier, Sulzfeld, all of Fed. Rep. of Germany

[73] Assignee: Gunther Krieg, Karlsruhe, Fed. Rep. of Germany

[21] Appl. No.: 905,470

[22] Filed: Jun. 29, 1992

[30] Foreign Application Priority Data

Jun. 28, 1991 [DE] Fed. Rep. of Germany ....... 4121429

[51] Int. Cl.$^5$ .............................................. B07C 5/02
[52] U.S. Cl. .................................... 209/3.1; 209/523; 73/23.22
[58] Field of Search ................ 209/522, 523, 3.1, 555, 209/556, 651, 644; 73/23.2, 23.22, 23.37, 863.92

[56] References Cited

U.S. PATENT DOCUMENTS

| 3,321,954 | 5/1967 | Bailey | 73/23 |
| 4,858,767 | 8/1989 | Myers et al. | 209/3.1 |

FOREIGN PATENT DOCUMENTS

| 254879 | 6/1987 | European Pat. Off. | |
| 8800862 | 2/1988 | European Pat. Off. | 209/523 |
| 4038993 | 6/1990 | Fed. Rep. of Germany | |
| WO88/00862 | 11/1988 | PCT Int'l Appl. | |

OTHER PUBLICATIONS

1369 Applied Spectroscopy 44 (1990) Jun., No. 5, Fredrick Me. US "A Novel Infrared Spectrometer Using a Linear Array Detector"–Hugh H. Richardson, et al.
812/Review of Scientific Instruments 60(1989) Sep. No. 9 New York, US "Signal Processing for an infrared array detector" M. S. Young, et al.
8008 TM Technisches Mossen 58 (1991) Marz No. 3 Munchen DE tm-Seri "Industrielle Gasanalyse" J. Staab.
Analytical Chemistry Bd. 62, Nr. 10, Mai 1990, Columbus US Seiten 1034–1043; J. J. Sullivan et al: 'Characterization of a Computerized Photodiode Array Spectrometer for gas chromatography-atomic emission Spectrometry'.
Applied Spectroscopy. Bd. 43, Nr. 1, Jan. 1989, Baltimore US Seiten 27–32; D. M. Mayes et al: 'A Photodiode-array Based Near-infrared Spectrophotometer for the 600-1100 nm Wavelength region'.

Primary Examiner—Kenneth W. Noland
Attorney, Agent, or Firm—Antonelli, Terry, Stout & Kraus

[57] ABSTRACT

For the effective, rapid, but still cost-effective, simple analysis of the content of containers, such as returned non-disposable drink bottles, the invention provides a method for examining the gas phases in containers, such as drink bottles, particularly for sorting and eliminating bottles in a drink bottle filling plant, in which a gas sample taken from the bottles is spectroscopically examined and the dispersed beam is detected by an array of juxtaposed detectors (detector array).

30 Claims, 7 Drawing Sheets

METHOD AND APPARATUS FOR EXAMINING THE GASEOUS CONTENT OF RETURNED DRINK BOTTLES

FIELD OF THE INVENTION

The invention relates to a method and an apparatus for examining the gaseous content of returned containers, particularly beverage or drink bottles, such as those made from plastics, in particular for sorting and eliminating bottles as a function of their content.

BACKGROUND OF THE INVENTION

The qualitative and quantitative detection and identification of pollutants in multiuse drink bottles, such as e.g. wood preservatives, multipurpose cleaners, oils, petrol, pesticides and other toxic substances, is an important problem for reasons of product loyalty, protection of human life, taste quality of drinks, environmental protection and the problems linked with the disposal of toxic substances. This problem more particularly occurs in connection with multiuse plastic bottles, e.g. those made from polyethylene and polycarbonate, because as a result of high diffusion coefficients the pollutants diffuse into the bottle walls. The pollutants are consequently not completely removed during the washing process and after refilling the bottle can diffuse back into the drink and have a negative influence on its taste.

The prior art does not solve the problem of detecting such pollutants in non-disposable or multiuse bottles. All that is commercially available is machines which, using photoionization detectors, which after removing a sample from the gas area of the bottle partly ionize this sample with ultraviolet radiation and measure the ion current occurring in an electric field, attempt to conclude whether any pollutants are present. However, as such photoionization detectors also detect harmless gases, such as e.g. water vapor, carbon dioxide, methane, etc., the ionization energy of the ultraviolet light must be so low that the substances are not indicated. As a result harmful pollutants, such as e.g. methanol, oils, diesel, ammonia, etc. also fail to be detected.

In addition, due to the high bottle capacities in the drinks industry of up to 50,000 bottles per hour and the resulting short measurement times per bottle, it is frequently necessary to have multiple sensor arrangements with up to forty sensor systems, which leads to unacceptably high costs for the overall system.

U.S. Pat. No. 4,858,767 refers to the use of mass spectrometers. However, such systems are only suitable to a limited extent for solving the problem, because the ionization necessary for mass selection also leads to a fragmentation of the molecules, so that the ionization products comprise other molecular compounds than the actual substances to be originally analysed. This more particularly occurs with the large molecules which appear in drinks or beverages, so that the measurement does not allow clear conclusions to be drawn regarding the toxicity or non-toxicity of the particular gaseous mixture. Both methods can lead to a contamination of the sensor, so that its effectiveness is reduced.

The solution to the problem proposed by U.S. Pat. No. 4,858,768 is that a bottle should be eliminated from the filling process if there are divergences compared with the pure drink. However, this is unacceptable for economic reasons, because divergences already exist if non-toxic substances are admixed with the drink, so that unobjectionable bottles are removed from the process.

It has generally already been proposed to investigate the gaseous content of returned drink bottles by infrared spectroscopy. However, conventional infrared spectroscopy does not generally have the desired resolution and is time-consuming, a high time requirement particularly resulting from the fact that a very large wavelength range must be covered due to the lack of high resolution.

WO-88/0862 proposes (IR) spectroscopy, without specifying the evaluation. Apart from the aforementioned disadvantages, an analysis of the total spectrum is too time-consuming or expensive. To the extent that spectroscopy in the near infrared between 1.1 and 2.5 $\mu$m is proposed, it has been found that this range is not sufficiently critical, i.e. the spectra in this range do not provide valid information, because they are not material-specific. In addition, the detection sensitivity in the near infrared is extremely low. Moreover, the necessary evaluation by regression analysis is time-consuming.

Admittedly, in the case of a Fourier transformation spectrometer detection takes place more rapidly, however, for the evaluation it is necessary to have expensive computers, which are economically unacceptable for the intended use, and the procedure is too slow for conventional drink filling plants due to the spectrum evaluation and comparison with specimen spectra.

SUMMARY OF THE INVENTION

The aim of the invention is to provide a method and an apparatus having high resolution, in order to be able to carry out the substance differentiation in a limited wavelength range and with a short measurement time.

According to the method of the invention, wherein a gas sample, removed from the bottle, is spectroscopically examined and the dispersed beam is detected by an array of juxtaposed detectors (detector array). According to the inventive apparatus, the spectrometer has an array of juxtaposed detectors (detector array 20), which are simultaneously illuminated by the dispersed light.

According to the invention bottles containing toxic substances are detected and removed from the drink filling line in non-destructive manner, i.e. without fragmentation of the toxic substances and are differentiated from those bottles only containing harmless fermentation products, such as e.g. result from residues of sweet drinks during the return transportation or the storage of the empty stock. Moreover, for the mineral water industry, the invention permits a distinction and selection between empty bottles which had been filled with sweet drinks and those which had contained mineral water, so as to ensure that sweet drink bottles are not filled with mineral water, which would impair the taste, because it is unavoidable that flavoring substances from the sweet drinks will diffuse from the bottle walls into the mineral water.

According to the invention, the examination of the gases removed from the drink bottles takes place exclusively in a wavelength range between 3 and 4 $\mu$m, because in this range detection sensitivity compared with the near infrared is better by a factor of about 10. Preferably, examination takes place in the range 3.2 to 3.6 $\mu$m.

Fundamentally bottles can be sorted and eliminated in two ways, separation taking place on the basis of whether the bottles contained toxic or unesthetic substances such as petrol, oils, diesel, isopropanol, urine, etc., or non-toxic substances and/or those substantially removable by cleaning, such as fermentation products, flavouring substances, air and mineral water vapour. Such a separation is suitable in those cases where bottles are filled with liquids containing flavors, such as lemonades and cola drinks, which conceal the flavours of said harmless substances. According to a particularly preferred development the bottles are separated in three ways, namely firstly toxic or unesthetic substances, said bottles being completely eliminated and destroyed. A further way can contain bottles with fermentation products and flavouring substances, said bottles being supplied for refilling with drinks containing flavouring substances. For the third way use is only made of bottles, which contained mineral water and the standard air components as gaseous substances and such bottles can be filled with mineral water. Bottles which contained harmless fermentation products or flavouring substances are not to be used for mineral water filling, because such residual flavours can conceal and falsify the taste of pure water, no matter whether it is still or carbon dioxide-containing mineral water.

According to a preferred development preferably working takes place with a resolution of better than 0.2 $\mu m$. According to a particularly preferred development the detector array contains a detector at 100 $\mu m$ and preferably the gap between two detectors of the array corresponds to the detector width. In order to increase the resolution here, according to a preferred development the detector array is displaced by the width of an individual detector of the array in the direction thereof. An outward and return displacement is adequate if the photosensitive gap between two detectors of the array is no greater than the width of the detectors. On choosing detector arrays with light-insensitive gaps, whose width is greater than that of the individual detectors, then it is possible to have a multiple displacement in one direction until the insensitive area of the detector array during the first measurement is completely covered by the further measurements performed after displacement.

According to an extremely preferred development, the height of the detectors perpendicular to the extension direction of the juxtaposed detectors of the array is greater than their width and in particular a multiple of the width. Thus, the necessary measurement time can be significantly reduced.

According to another preferred development, the element bringing about the dispersion is a grating, particularly a reflection grating and preferably a blazed grating. This is a grating with juxtaposed micromirrors inclined from the grating plane by a given angle, so that the first order maxima in which a dispersion takes place have an adequate and higher intensity than occurs with a conventional grating. In another preferred development a holographic grating is used.

For reducing noise in the reception area, namely of the detector and electronic noise, the detector and electronics are cooled and in particular the detector can be cooled by means of a Peltier member.

For eliminating environmental influences and remaining noise, according to a preferred development the emitted light is timed or intensity-modulated. This can take place with a Planckian radiator of limited thermal capacity, such as a wire or a thin conductive coating in an electronic manner, or in the case of slow light sources, such as infrared diodes, by a mechanical chopper, the signal processing being carried out by a lock-in amplifier.

BRIEF DESCRIPTION OF THE DRAWINGS

The invention is described in greater detail hereinafter relative to the drawings, wherein.

Figure 1:
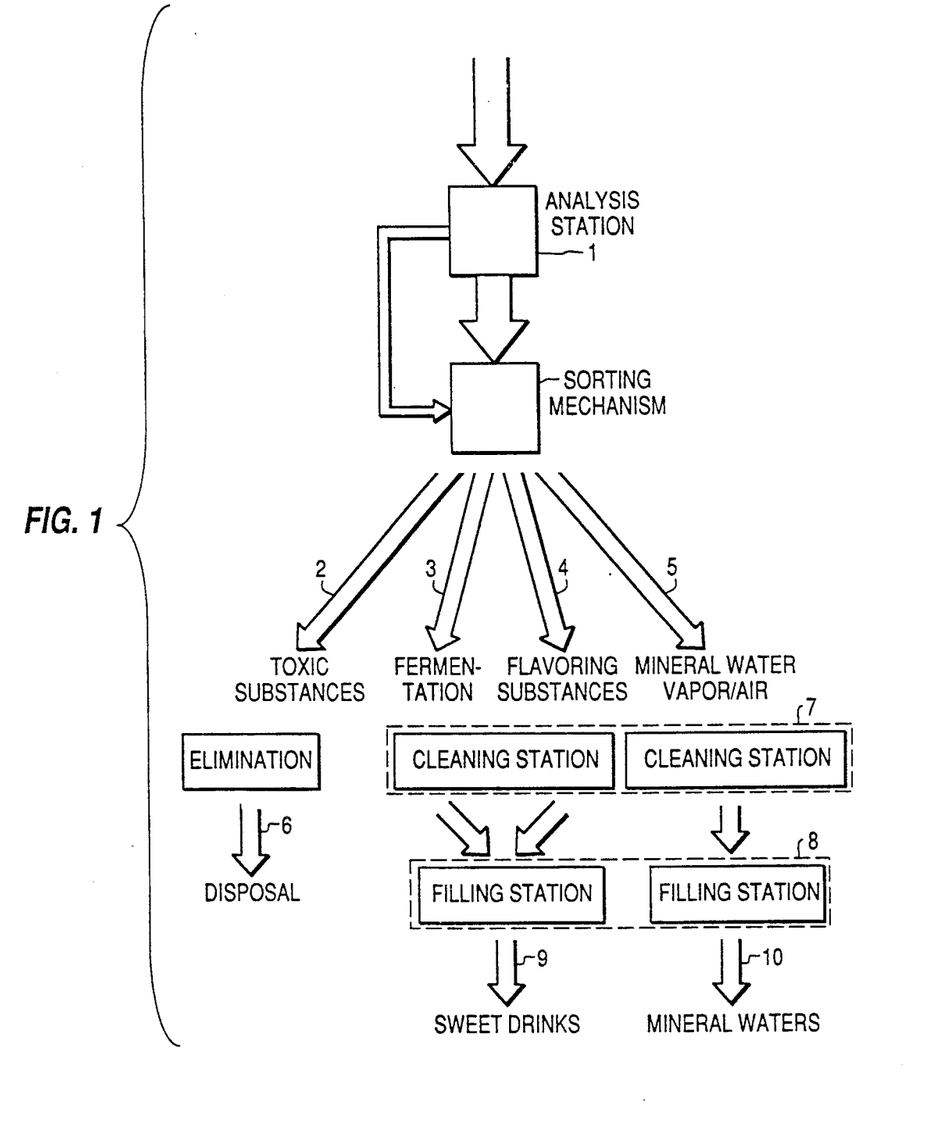
FIG. 1 is a schematic view of an overall system for examining a gaseous content of returned models and classifying the same into different categories.

According to FIG. 1 the gas contents of non-disposable bottles are analysed in non-destructive manner in an analysis station 1. According to the result of the on-line analysis, the bottles are classified in accordance with their gas contents into toxic substances 2, fermentation products 3, flavoring substances 4, air/mineral water vapor 5. The bottles containing toxic substances 2 are eliminated and automatically disposed of. The remaining bottles pass through a cleaning station 7 and subsequently pass into the drink or beverage filling stations 8. The bottles which contained fermentation products or flavouring substances are supplied to the sweet drinks line 9; whereas, the bottles which contained air and water vapor 5 pass into the mineral water line 10.

Figure 2:
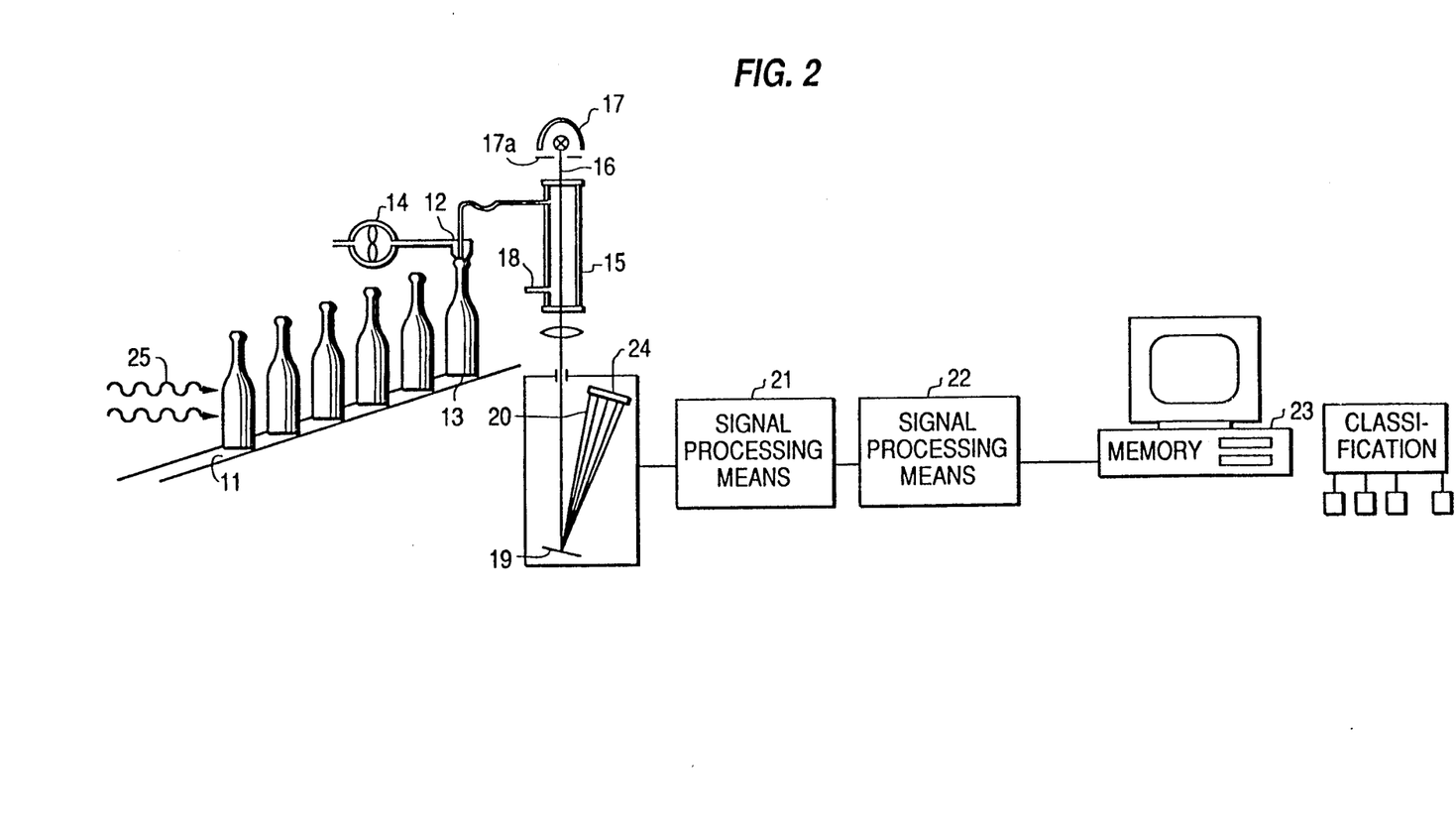
FIG. 2 is a schematic view of an embodiment of the present invention for optoelectronic classification to different categories.

According to FIG. 2 the bottles are supplied mechanically by a transportation mechanism 11 to the classification system. The transportation system comprises a high speed sampler 12, which removes a gas sample from the particular bottle 13 in that, by a pressure unit or pump 14, a gas volume is supplied to the inspection or examination chamber 15. Alternatively, the pump 14 can also be fitted to connecting pieces 18, so that sampling takes place by a suction process. The examination chamber 15 is timed by a chopper 17a and then broken down into its spectral components by a dispersion unit 19. The spectral distribution is detected by a plurality of linear sensor elements 20 and microelectronically processed by following signal processing means 21, 22.

Figure 2A:
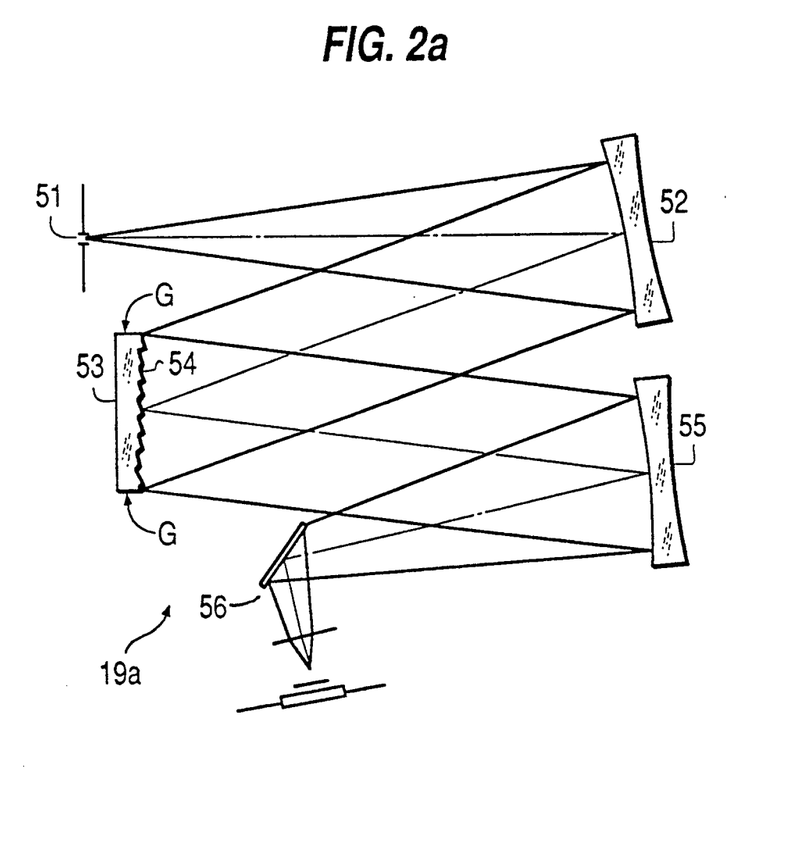
FIG. 2a is a schematic detail view of the optical construction of the embodiment of FIG. 2.

FIG. 2a shows the optical construction shown only in general terms in FIG. 2. The beam passing out of the examination chamber or cell 15 passes through an entrance slit 51 into the spectrometer 19a and is parallelized by a first concave mirror 52 (imaging into infinity). Preferably, optical gratings or prisms are used as dispersion units 19. In the represented embodiment the parallel beam strikes a spectral dispersion element in the form of a blazed grating 53, which compared with a conventional reflection grating, does not have aligned reflecting faces (with non-reflecting areas between them), but instead mirrors 54 inclined from the grating plane G by a blaze angle. Therefore, the incident light is preferably reflected in one direction with a finite path difference. This makes it possible for the first order maxima of the spectral dispersion to bring about a higher intensity than with a conventional grating, in which the non-dispersed zero order maximum contains the preponderant intensity.

The beam dispersed by the grating 53 is then imaged on the detector array 20 cooled by means of Peltier members 24 is then imaged by means of a lens 1' by a further concave mirror 55 via a reflecting mirror 56. In the case of a compact construction, said imaging optics leads to a good imaging of the entrance slit 51, particularly with respect to its width, on the detector array 20 (as a function of the "color").

A signal processor system 48 (FIG. 6) determines the spectral distribution and compares the spectral distribution with the spectra filed in a memory 23, so that there is clear identification of the substances involved.

Figure 4A:
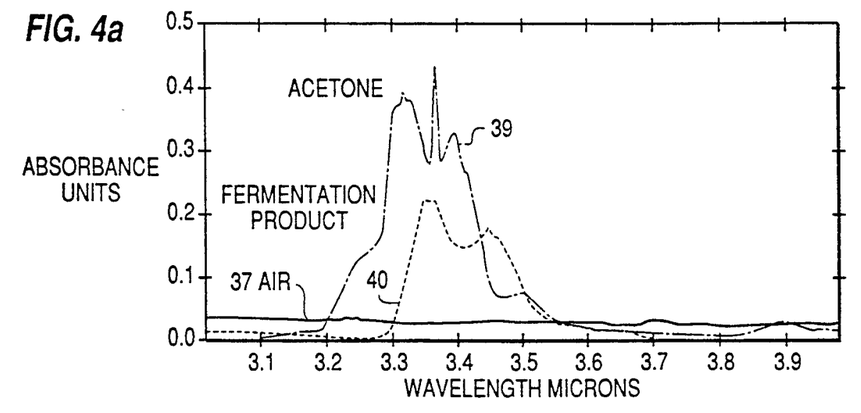
FIGS. 4a-4c are graphical illustrations of a spectrum of ambient air, as well as a spectrum of sweet drinks, pollutants and fermentation products.
Figure 4B:
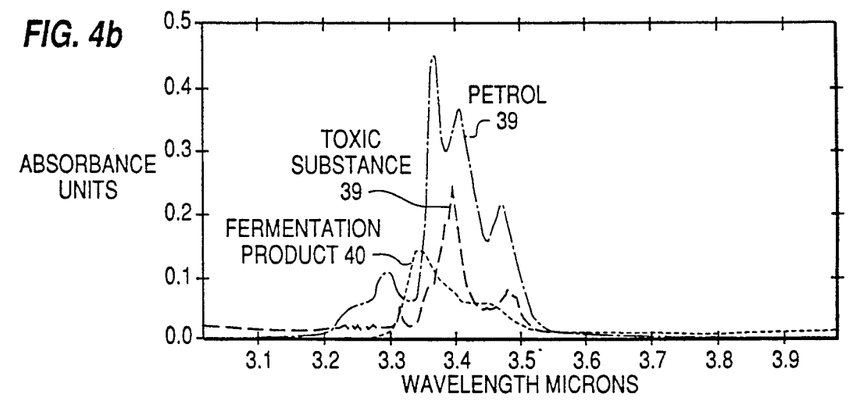
Figure 4C:
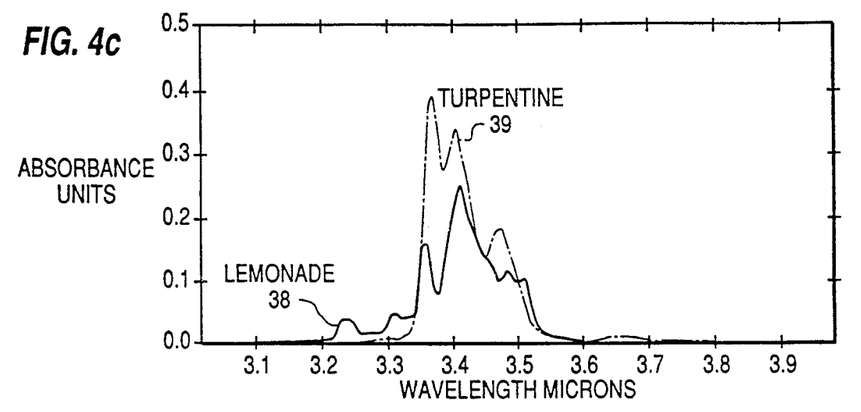

The sensor elements 20 in the infrared range are arrays of photocells made from silicon or mercury-cadmium-telluride (MCT) semiconductor compounds. PbSe sensors can also be used. The individual sensors have a width in their extension direction in the μm range of e.g. 50 μm. The gap between the sensors is preferably of the same order of magnitude. In the case of a 50 μm gap, i.e. detector spacing (center-to-center) of 100 μm, a detector array of 32 detector elements has a length of 3.2 mm. It has been found that the spectral range between 3.2 and 3.6 μm is a particularly characteristic spectral cutout for the sought use, as can be gathered from FIGS. 4a to 4c. Following spectral dispersion this spectral range is imaged on the detector array of 3.2 mm and therefore on the 32 detector elements. For increasing the measurement points, according to a preferred development, the detector array can be displaced by half the 100 μm distance, i.e. by 50 μm (corresponding to the gap width), so that the light striking in this area is also detected.

Preferably the sensor elements have a length at right angles to the stringing together, which considerably exceeds the width thereof and is here 1.5 mm, so as to receive adequate light quantities in the case of the low intensity of the incident light due to the necessary resolution. This more particularly applies because with the optics used although the gap width is well imaged, its length is distorted. For improving the radiation detection these detectors are cooled with three-stage Peltier members 24 to temperatures below −70° C. The substance identification inventively takes place in such a way that spectra of ambient air 37 according to FIG. 4 are subtracted from the presently measured spectra 38, 39, 40 of sweet drinks, pollutants and fermentation products and the result of the subtraction is compared with the spectra filed in the memory 23, so that it is possible to identify the pollutants with respect to the particular molecular compound and also the pollutant concentration.

Figure 5:
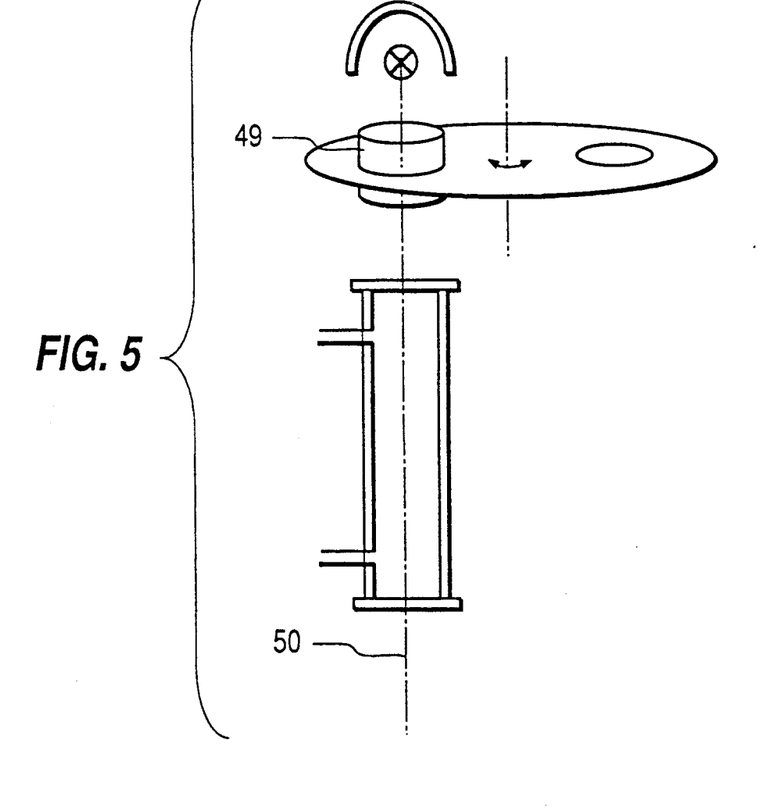
FIG. 5 is an exploded view of a test cell which can be pivoted into the optical path for the wavelength calibration of the detector array.

In order to e.g. correct temperature-caused changes in the wavelength scale, according to FIG. 5 a test cell 49 filled with test gas, e.g. methane is at certain times pivoted into the optical path. From the physically known position of the spectral lines of the test gas on the wavelength scale, it is possible to derive a recalibration of the particular detector element position, e.g. by interpolation.

Figure 6:
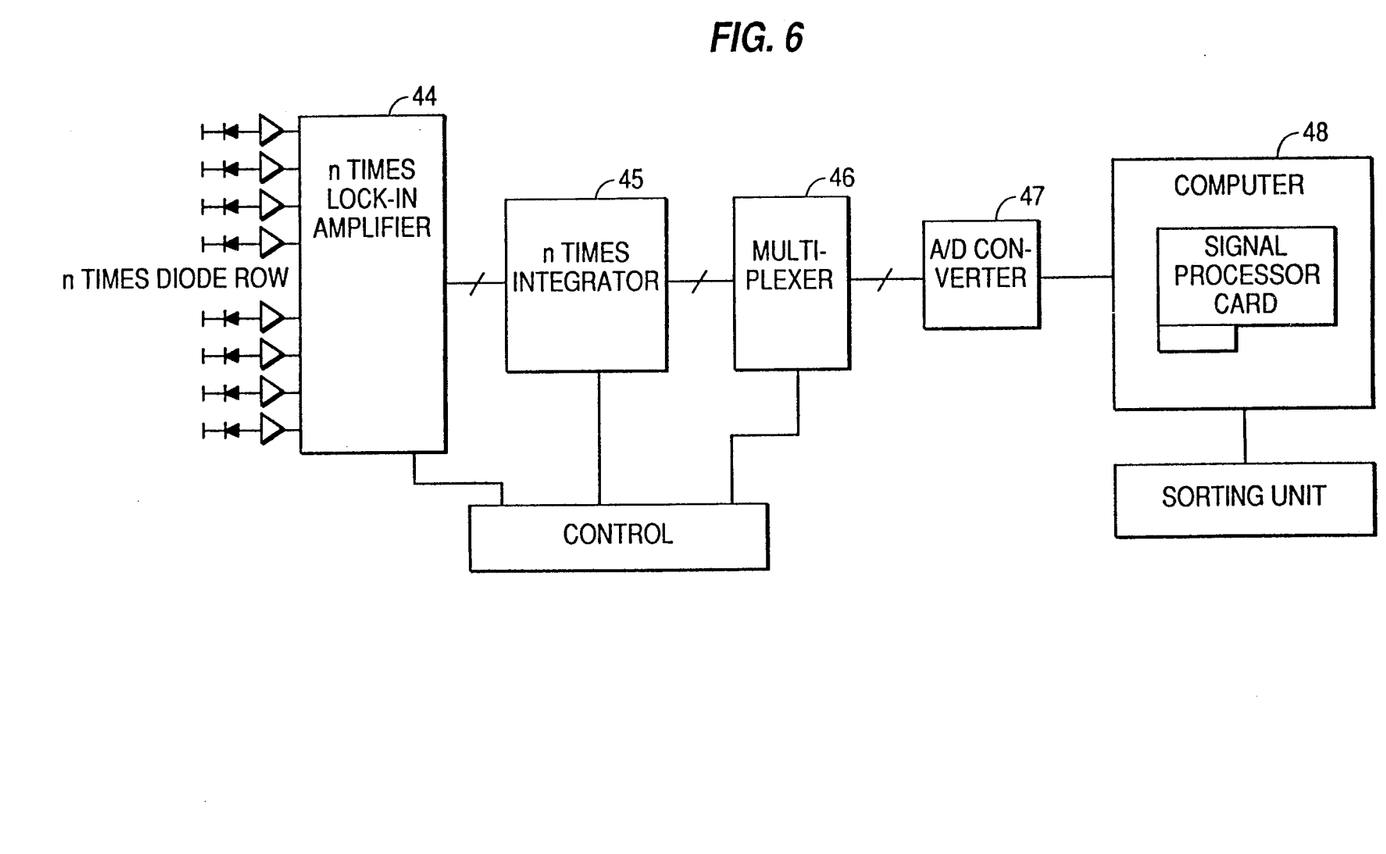
FIG. 6 is a block circuit diagram of electronic signal processing equipment for effecting the method and apparatus of the present invention.

The radiation of different wavelength ranges striking the array detector elements 43 periodically following electronic or mechanical modulation is, according to FIG. 6, further processed by n parallel lockin amplifiers 44, which are synchronized with the modulation mechanism, as well as by n parallel, time-controlled integrators 45. By a multiplexer 46 and an A/D converter 47, the measured values are supplied to the central computing system 48 for final processing and for initiating control processes.

In order to be able to detect relatively complicated spectra according to FIG. 4 with a sufficiently large number of measurement point pairs with, at the same time, a comparatively small number of individual detectors (pixels) in the detector array, according to a further development of the invention a micromechanical displacement of the sensor array 20 is provided, the displacement being so chosen that the pixels assume positions which are between the original position of two pixels. Preferably, a piezotranslator is used for displacement purposes. This effect can also be obtained by a slight tilting of the dispersion element 19 about a rotation axis.

For increasing the sensitivity of the substance detection the partial pressure of the substances to be detected is preferably increased by radiating in infrared light 25 or microwave radiation according to FIG. 2, in that the molecules absorbed in the bottle walls are released therefrom by energy supply and diffuse into the gas area.

Figure 3A:
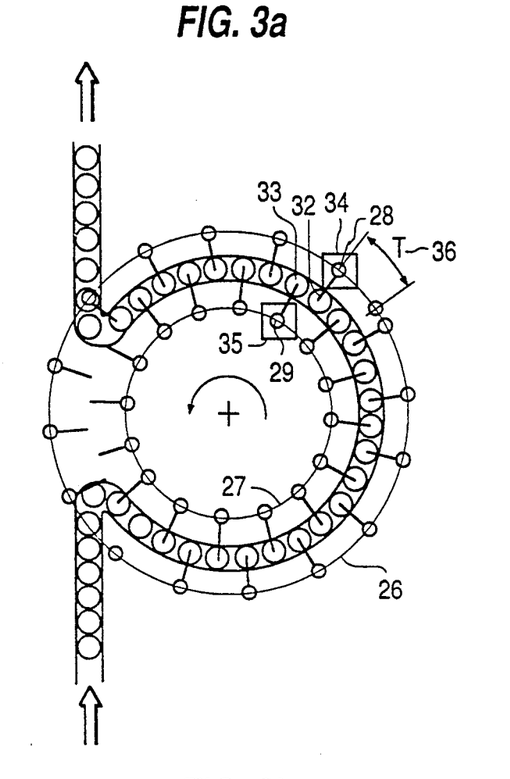
FIGS. 3a-3b are schematic views of an embodiment for further increasing a bottle capacity of drink filling plants, while simultaneously maintaining classification qualities.
Figure 3B:
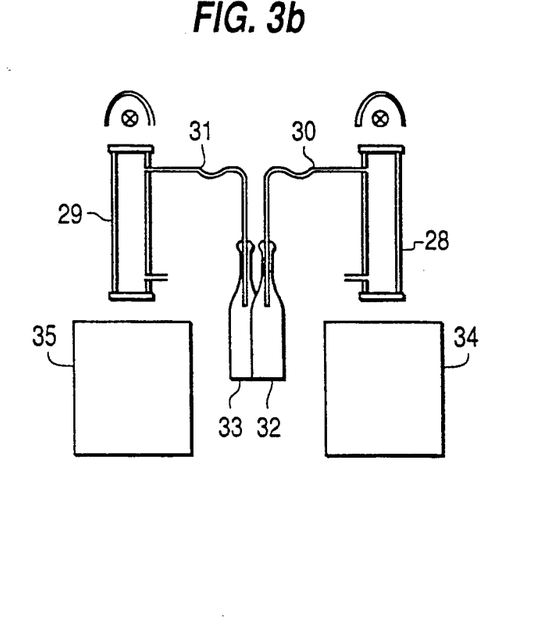

In order to solve the problem of the short cycle times per bottle, which is due to very high bottle flow rates of up to 50,000 bottles per hour, according to a special development of the invention, preferably, more than one high speed detector array system according to FIG. 2 is used, as well as for reducing the mechanical loading and wear to the machine use is also made of the system shown in FIGS. 3a and 3b.

The gas samples taken from the bottles 32, 33 arriving on the transportation system 11 according to FIG. 2 are introduced by equal length, flexible lines 30, 31, alternately into the measurement cells 28, 29 travelling on the outer path 26 and the inner path 27. In the vicinity of the stationary analysis modules 34, 35, according to the invention the measurement cells 28, 29 are stopped for the measurement time T36, so that an adequate analysis time is ensured even with this high clock rate.

Furthermore, there may be provided one or more test cells filled in defined manner with a specific test gas, as methane, vapor of isopropylalcohol ($CH_3CH(OH)CH_3$ 2-propanol), gasoline, ethanol or the like, with each test cell having a defined length traversed by the light and, accordingly, a defined extinction. Such cells may be pivoted in the optical path in order to examine and calibrate the optical detector. Alternatively, chambers, as the examination chambers 15, may be filled with such a test gas and provided in the conveyer for the measurement chambers (in exchange with the measurement chambers) in order to examine or calibrate the detector.

We claim:

1. Method for examining gas phases in containers, such as drink or beverage bottles, particularly for sorting and eliminating bottles in a drink bottle filling plant, the method comprising the steps of removing a gas sample from the bottles, examining the gas sample by spectroscopy by passing an IR light beam through the gas sample, directing the spectroscopically widened beam to a detector array of juxtaposed detectors, wherein a wavelength range of approximately 3.2 to 3.6 μm is received by the detector array and then examined, subdividing the containers in accordance with substances detected by the detector array over at least two transportation paths, wherein the containers containing an unknown, undefinable substance or toxic substance is supplied to one transportation path and containers exclusively containing water vapor or air are supplied to the other transportation path, and wherein containers found to contain harmless fermentation products or flavoring substances are supplied to the first transportation path.

2. Method for examining gas phases in containers, such as drink or beverage bottles, particularly for sorting and eliminating bottles in a drink bottle filling plant, the method comprising the steps of removing a gas sample from the bottles, examining the gas sample by spectroscopy by passing an IR light beam through the gas sample, directing the spectroscopically widened beam to a detector array of juxtaposed detectors, wherein a wavelength range of approximately 3.2 to 3.6 µm is received by the detector array and then examined, subdividing the containers in accordance with substances detected by the detector array over at least two transportation paths, wherein the containers containing an unknown, undefinable substance or toxic substance is supplied to one transportation path and containers exclusively containing water vapor or air are supplied to the other transportation path, and wherein containers found to contain harmless fermentation products or flavoring substances are supplied to the second transportation path.

3. Method according to one of claims 1 or 2, wherein a spectral resolution is greater than 0.02 µm.

4. Method according to one of claims 1 or 2, wherein gas spectra are detected with a detector array of HgCdTe or PbSe photocells.

5. Method according to one of claims 1 or 2, wherein the detector array is cooled by a Peltier member in at least a single-stage.

6. Method according to one of claims 1 or 2, wherein a substance identification and concentration determination takes place by a real time comparison of a measured spectra and known spectra located in a memory.

7. Method according to one of claims 1 or 2, wherein individual detectors of the detector array are brought, by a micromechanical displacement mechanism, periodically along a detection direction of the detector array to positions between a starting position of two individual detectors.

8. Method according to one of claims 1 or 2, wherein there is a cyclic wavelength calibration of the detector array by introducing a test gas into the optical path.

9. Method according to one of claims 1 or 2, wherein a partial vapor pressure of a gas phase is increased by heating the bottle walls or the molecules on the bottle walls by infrared or microwave radiation.

10. Method according to claim 1, wherein test cells receiving gas samples are moved with the containers along an outer and an inner path.

11. Method for examining gas phases in containers, such as drink or beverage containers, particularly for sorting and eliminating bottles in a drink bottle filling plant, the method comprising the steps of removing a gas sample from the bottles, examining the gas sample by IR spectroscopy by passing an IR light beam through the gas sample, and directing the spectroscopically widened beam to a detector array of juxtaposed detectors, wherein a wavelength range of approximately 3.2 to 3.6 µm is received by the detector array and then examined, and wherein the containers are supplied to at least three transportation paths for respectively receiving toxic substances, unknown and undefinable products, harmless fermentation products and flavoring substances, and mineral water vapor and air.

12. Method according to claim 11, wherein bottles containing toxic substances, unknown and undefinable substances are eliminated and disposed of, whereas bottles containing fermentation products and/or flavoring substances are cleaned and supplied to a soft drink filling plant.

13. Method according to claim 11, wherein containers which only contain mineral water vapor and/or air are, after cleaning, supplied to a mineral water filling plant.

14. Method for examining gas phases in containers, such as drink or beverage bottles, particularly for sorting and eliminating bottles in a drink bottle filling plant, the method comprising the steps of removing a gas sample from the bottles, examining the gas sample by IR spectroscopy by passing an IR light beam through the gas sample, and directing the spectroscopically widened beam to a detector array of juxtaposed detectors, wherein a wavelength range of approximately 3.2 to 3.6 µm is received by the detector array and then examined, test cells receiving the gas samples are moved with the containers along an outer and inner path, and wherein the containers receiving the gas samples are alternately filled into the test cells in the outer and inner paths by equal length flexible lines.

15. Method for examining gas phases in containers, such as drink or beverage bottles, particularly for sorting and eliminating bottles in a drink bottle filling plant, the method comprising the steps of removing a gas sample from the bottles, examining the gas sample by IR spectroscopy by passing an IR light beam through the gas sample, and directing the spectroscopically widened beam to a detector array of juxtaposed detectors, wherein a wavelength range of approximately 3.2 to 3.6 µm is received by the detector array and then examined, test cells receiving the gas samples are moved with the containers along an outer and inner path, and wherein a gas content of the gas samples of the test cells in the outer and inner paths is simultaneously analyzed by individual analysis stations.

16. Method for examining gas phases in containers, such as drink or beverage bottles, particularly for sorting and eliminating bottles in a drink bottle filling plant, the method comprising the steps of removing a gas sample from the bottles, examining the gas sample by IR spectroscopy by passing an IR light beam through the gas sample, and directing the spectroscopically widened beam to a detector array of juxtaposed detectors, wherein a wavelength range of approximately 3.2 to 3.6 µm is received by the detector array, and wherein test cells are stopped in a vicinity of analysis stations for a measurement time, without impairing a continuous bottle transport.

17. Apparatus for examining gas phases in containers, such as drink or beverage bottles, particularly for sorting and eliminating bottles in a drink bottle filling plant, with test cells for receiving a gas sample from a container and with an IR spectrometer in which the radiation passing through the gas sample is dispersed, wherein the IR spectrometer has an array of juxtaposed detectors, the array is simultaneously illuminated by a dispersed light of a wavelength in a range of approximately 3.2 to 3.6 µm, two transportation paths are provided behind an examination station for the containers, containers supplied to the first transportation path contained unknown, undefinable or toxic substances, containers supplied to the second transportation path contained mineral water, vapor or air, and wherein containers containing harmless fermentation products and flavoring substances are supplied to the second transportation path.

18. Apparatus for examining gas phases in containers, such as drink or beverage bottles, particularly for sorting and eliminating bottles in a drink bottle filling plant, with test cells for receiving a gas sample from a container and with an IR spectrometer in which the radiation passing through the gas sample is dispersed, wherein the IR spectrometer has an array of juxtaposed detectors, the array is simultaneously illuminated by a dispersed light of a wavelength in a range of approximately 3.2 to 3.6 µm, and wherein three separate transportation paths are provided for respectively transporting unknown, undefinable toxic substances, harmless fermentation products and flavoring substances, and mineral water vapor and air.

19. Apparatus according to one of claims 17 or 18, wherein a device is provided for classifying in different pollutant classes by quantitative measurement of the IR and/or UV absorption of the gas phases.

20. Apparatus according to one of claims 17 or 18, wherein the spectral resolution capacity of the infrared spectrometer is greater than 0.02 µm.

21. Apparatus according to one of claims 17 or 18, wherein a Peltier cooling mechanism is in thermal contact with the detector array.

22. Aparatus for examining gas in containers, such as drink or beverage bottles, particularly for sorting and eliminating bottles in a drink bottle filling plant, with test cells for receiving a gas sample from a container and with an IR spectrometer in which the radiation passing through the gas sample is dispersed, wherein the IR spectrometer has an array of juxtaposed detectors, the array is simultaneously illuminated by a dispersed light of a wavelength in a range of approximately 3.2 to 3.6 µm, and wherein the detector array includes HgCdTe or PbSe photocells.

23. Apparatus for examining gas in containers, such as drink or beverage bottles, particularly for sorting and eliminating bottles in a drink bottle filling plant, with test cells for receiving a gas sample from a container and with an IR spectrometer in which the radiation passing through the gas sample is dispersed, wherein the IR spectrometer has an array of juxtaposed detectors, the array is simultaneously illuminated by a dispersed light of a wavelength in a range of approximately 3.2 to 3.6 µm, and wherein a substance identification and concentration determination device using real time comparison of a measured spectra and spectra in a memory is provided.

24. Apparatus for examining gas in containers, such as drink or beverage bottles, particularly for sorting and eliminating bottles in a drink bottle filling plant, with test cells for receiving a gas sample from a container and with an IR spectrometer in which the radiation passing through the gas sample is dispersed, wherein the IR spectrometer has an array of juxtaposed detectors, the array is simultaneously illuminated by a dispersed light of a wavelength in a range of approximately 3.2 to 3.6 µm, and wherein a micromechanical displacement device is provided for a displacement of the individual detectors of the detector array in a periodic manner along an extension direction of the detector array to positions between starting positions of, in each case, two individual detectors.

25. Apparatus for examining gas in containers, such as drink or beverage bottles, particularly for sorting and eliminating bottles in a drink bottle filling plant, with test cells for receiving a gas sample from a container and with an IR spectrometer in which the radiation passing through the gas sample is dispersed, wherein the IR spectrometer has an array of juxtaposed detectors, the array is simultaneously illuminated by a dispersed light of a wavelength in a range of approximately 3.2 to 3.6 µm, and wherein a device is provided for enabling a cyclic wavelength calibration of the detectors by introducing a test gas into an optical path.

26. Apparatus for examining gas in containers, such as drink or beverage bottles, particularly for sorting and eliminating bottles in a drink bottle filling plant, with test cells for receiving a gas sample from a container and with an IR spectrometer in which the radiation passing through the gas sample is dispersed, wherein the IR spectrometer has an array of juxtaposed detectors, the array is simultaneously illuminated by a dispersed light of a wavelength in a range of approximately 3.2 to 3.6 µm, and wherein a device is provided for increasing a partial vapor pressure of the gas phase by heating container walls with infrared radiation or microwave radiation.

27. Apparatus for examining gas in containers, such as drink or beverage bottles, particularly for sorting and eliminating bottles in a drink bottle filling plant, with test cells for receiving a gas sample from a container and with an IR spectrometer in which the radiation passing through the gas sample is dispersed, wherein the IR spectrometer has an array of juxtaposed detectors, the array is simultaneously illuminated by a dispersed light of a wavelength in a range of approximately 3.2 to 3.6 µm, and wherein the test cells are arranged in a double manner, namely, on an outer path and on an inner path and can be moved together with transported containers.

28. Apparatus according to claim 27, further comprising equal length flexible lines for alternate filling of gas samples from incoming containers into the outer and inner test cells.

29. Apparatus according to claim 27, further comprising two analysis stations for enabling a simultaneous analysis of a gas content of the outer test cell and the inner test cell.

30. Apparatus for examining gas in containers, such as drink or beverage bottles, particularly for sorting and eliminating bottles in a drink bottle filling plant, with test cells for receiving a gas sample from a container and with an IR spectrometer in which the radiation passing through the gas sample is dispersed, wherein the IR spectrometer has an array of juxtaposed detectors, the array is simultaneously illuminated by a dispersed light of a wavelength in a range of approximately 3.2 to 3.6 µm, and wherein the test cells can be stopped in a vicinity of analysis stations for a measurement time without impairing a continuous bottle transport.

* * * * *